United States Patent [19]

DiLeo et al.

[11] Patent Number: 5,339,675
[45] Date of Patent: Aug. 23, 1994

[54] APPARATUS FOR MONITORING IMPURITIES IN A GAS STREAM

[75] Inventors: Anthony J. DiLeo, Westford, Mass.; James T. Snow; Daniel A. Cote, both of Nashua, N.H.

[73] Assignee: Millipore Corporation, Bedford, Mass.

[21] Appl. No.: 958,384

[22] Filed: Oct. 8, 1992

[51] Int. Cl.⁵ .................................. G01N 29/02
[52] U.S. Cl. .................. 73/24.040; 73/24.06
[58] Field of Search ............ 73/24.01, 24.03, 24.04, 73/31.06, 24.06

[56] References Cited

U.S. PATENT DOCUMENTS

| | | | |
|---|---|---|---|
| 3,164,004 | 1/1965 | King, Jr. | 73/24.06 |
| 3,385,100 | 5/1968 | Michael | 73/24.01 |
| 3,427,864 | 2/1969 | King, Jr. | 73/24.04 |
| 3,478,573 | 11/1969 | King, Jr. | 73/24.04 |
| 3,534,585 | 10/1970 | Webb | 73/24.04 |
| 3,744,296 | 7/1973 | Beltzer | 73/24.01 |
| 4,312,228 | 1/1982 | Wohlfjen | 73/24.01 |
| 4,681,855 | 7/1987 | Huang | 73/24.04 |
| 4,860,573 | 8/1989 | Barendz et al. | 73/24.01 |
| 5,042,288 | 8/1991 | Vig | 73/24.01 |
| 5,065,140 | 11/1991 | Neuburger | 73/24.04 |
| 5,120,505 | 6/1992 | Lowell, Jr. et al. | 436/150 |

FOREIGN PATENT DOCUMENTS 3-102238  9/1989  Japan ............... 73/24.04

Primary Examiner—Timothy M. McMahon
Attorney, Agent, or Firm—Paul J. Cook; Andrew T. Karnakis

[57] ABSTRACT

A device is provided comprising a piezoelectric material and at least one coating reactive with trace quantities of oxygen and/or water in reactive and inert gases. The piezoelectric material is bonded to a conductor for delivering an alternating electric current and to a conductor for transmitting resonant vibration frequency of the crystal. The reactive coating has an effective thickness which provides a serviceable life for the coating while not being so thick as to prevent vibration of the piezoelectric material.

26 Claims, 5 Drawing Sheets

APPARATUS FOR MONITORING IMPURITIES IN A GAS STREAM

BACKGROUND OF THE INVENTION

This invention relates to a method and apparatus for detecting oxygen and/or water impurities in a gas stream. More particularly, this invention relates to a method and apparatus for detecting oxygen and/or water impurities utilizing a coated piezoelectric crystal.

At the present time ultrapure gas streams are utilized in chemical reactions such as in the semiconductor industry. These chemical reactions usually are conducted in sealed containers to maintain purity since the gases often times are toxic and are conducted under low pressure in order to decrease the probability of unwanted side reactions. In order to maintain the requisite gas purity, the gas is treated, prior to entering the reaction chamber, in order to remove impurities therefrom. It is general practice to pass the gas through a bed of resin particles which are interactive with impurities such as with oxygen and water in the gas. Over time, the capacity of the bed of resin particles for interacting with the impurities is depleted to a point where breakthrough of impurities from the resin bed occurs and the impurities enter the reaction zone. It is difficult to predict when undesirable depletion of resin capacity occurs so that in the absence of independent monitoring means, premature or late removal of the resin is likely. Premature resin removal results in increased resin cost while late removal results in expensive damage to reaction product.

It has been proposed in U.S. Pat. No. 5,138,867 to provide a detection system for sensing concentration of impurities in a gas stream which includes a sensing device which can be hygrometric, spectrophotometric, piezoelectric or colorimetric. The specific piezoelectric device disclosed is a surface acoustical wave (SAW) device. In a SAW device, an acoustical wave is passed along a surface coating on a substrate to measure the change in mass at the interface between the coating and the substrate. Mass change in the coating is caused by reaction of the coating with impurities in a gas which contacts the coating. Accordingly, a reactive polymer coating material is described that is consumed over time and regenerable. In the SAW device, the coating must be thin; on the order of a wavelength of the acoustic wave or thinner in order to permit accurate measurement of impurity concentration. While this device is extremely sensitive to impurity concentration change, i.e. in the picogram level, it is too sensitive for use in a device requiring an extended service, i.e., about one year or more, since the thickness of the coating necessary to have the capacity for extended lifetimes quickly exceeds that which permits accurate measurements.

A scavenger for oxygen and water vapor impurities comprising metal hydrides are disclosed in U.S. Pat. Nos. 4,950,419 and 4,716,181.

It would be desirable to provide a means for detecting impurities in a gas stream which is useful and accurate for extended times. In addition, it would be desirable to provide such a means for detecting impurities capable of quantifying impurity concentration in a gas.

SUMMARY OF THE INVENTION

The present invention provides a coated piezoelectric apparatus for detecting the presence of oxidant and/or water impurities in a wide variety of gases. A piezoelectric crystal is coated on one or more opposing surfaces with a metal, metal hydride or metal halide which is reactive with oxygen and/or with water. The mass of coating applied is large enough so that there is enough material to continue to react with oxygen and/or water for the service lifetime that is desired, while not being so heavy as to prevent or substantially reduce vibration of the piezoelectric crystal due to its mass or the mass of the reaction product. The crystal is subjected to an alternating electric field and the resonant vibration caused by the electric field is detected. Reaction of water and/or oxygen with the reactive coating will form a reaction product with an accompanying change of mass. The mass change will cause a change in resonant frequency, i.e., a mass increase causes a resonant frequency decrease due to a damping effect which is measured. The resonant frequency measured can be correlated to water and oxygen impurity concentration in the incoming gas by means of a standard curve. The piezoelectric crystal can be coated with a protective polymer such as poly(vinylidene fluoride) (PVDF) or polytetrafluoroethylene to protect the piezoelectric from corrosive gases such as hydrogen fluoride. The reactive coating is coated on the protective polymer. The combined mass of the two coatings must meet the mass criteria set forth above.

DESCRIPTION OF SPECIFIC EMBODIMENTS

Figure 8:
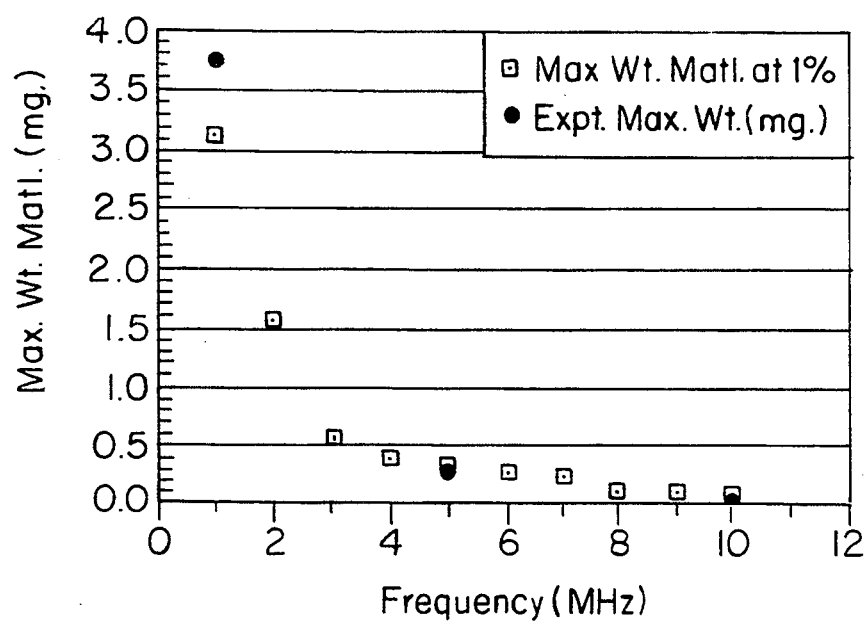
FIG. 8 illustrates the selection of the maximum weight of coating mass assuming a 1% Fo for crystal linear range.

The coated piezoelectric crystals of this invention comprise a piezoelectric substrate such as natural quartz, lithium niobate, lead metaniobate, lead zirconate titanate, poly(vinylidene difluoride) (PVDF), Rochelle salts, tormaline, ethylenediamine tartrate, dipotassium tartrate, ammonium dihydrogen phosphate or the like, preferably quartz (and PVDF in hydrogen fluoride gas streams). The coating is applied to one or both of the largest surfaces of the substrate. The behavior of the piezoelectric crystals can be explained using the Sauerbrey equation:

$$\Delta f = -f_0^2 m / NA\rho$$

where $\Delta f$ is the observed frequency change, $f_O$ is the fundamental frequency of the crystal, m is the mass change at the electrode surface, N is the frequency constant for the crystal, A is the surface area of the deposit, and $\rho$ is the density of the piezoelectric crystal. As evidenced by the equation, the observed frequency change is linearly dependent on the mass change but varies to the square of the fundamental frequency. Thus, a 2.0-MHz crystal will be four times more sensitive than 1.0-MHz crystal. Good correlation has been found between the observed and calculated frequency change when the crystal linear range is assumed to be 1% of $F_O$ as shown in FIG. 8. Outside this range, this linear relationship between frequency and mass change will deteriorate and above a critical mass, the crystal will cease to oscillate. Thus, as shown in FIG. 8, the maximum amount of material that the crystal can accommodate and still vibrate within the linear response range will vary according to the frequency of the piezoelectric crystals utilized and is generally between about 1 and 3.5 micrograms. The minimum amount of coating on the crystal dictated by the capacity necessary to permit operation within an acceptable lifetime, e.g., ca. 45 micrograms for one year service life at a constant impurity of 1 ppb. This minimum mass loading varies with the desired lifetime and impurity concentration in accordance with:

$$\text{mass}/45 = \sqrt{C*t}$$

where: mass is in micrograms
C is impurity concentration in units of ppb
t is lifetime in units of years
When the reactive coating mass is below this amount the device is useful only for a period of time until the reactive sites are consumed. The minimum mass is referred to herein as the "effective mass".

Suitable coatings are those which react with both oxygen and/or water, permit detection of oxygen and/or water at concentrations of 1 part per billion (ppb) and do not add contaminant to purified gas. The coatings most useful in the present invention are pure metal or metal hydride coatings. Representative suitable metals include lithium, magnesium, potassium, strontium, barium, sodium, calcium, or the like. Representative suitable metal hydride coatings include lithium hydride, magnesium hydride, sodium hydride, lithium aluminum hydride or the like. Representative suitable metal halide coatings include magnesium chloride, magnesium bromide, aluminum fluoride or the like. It is preferred to utilize metals having low molecular weight or metal hydrides formed of a metal having a low molecular weight such as lithium or magnesium since the mass change as a result of reaction with water or oxygen is larger and more easily detectable as compared to coatings containing higher molecular weight metals.

The detector of this invention is useful in monitoring impurity concentration in inert gases, such as helium, argon, nitrogen; silicon containing gases such as silane, dichlorosilane, trichlorosilane; dopants such as arsine, phosphine, diborane; etchants such as halocarbon 14, halocarbon 16, halocarbon 218, sulfur hexafluoride, chlorine, hydrogen bromide or reactants such as hydrogen chloride, hydrogen fluoride or ammonia. When monitoring a halogenated gas, the metal or metal hydride is first converted to a metal halide by the gas stream which then is reactive with water vapor to produce the effects discussed above. The mass change corresponding to this conversion must not exceed the maximum mass specified for the crystal discussed above. Alternatively, the metal halide may be deposited on the piezoelectric crystal by a suitable thin film deposition technique.

Figure 1:
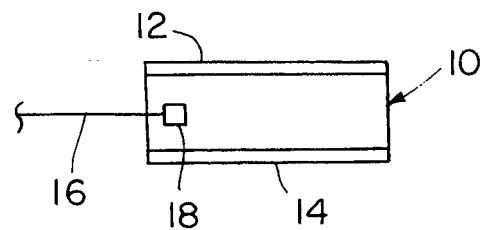
FIG. 1 is a side view of a coated piezoelectric crystal device of this invention.

Referring to FIG. 1, the composite structure of this invention includes a piezoelectric crystal which is coated with the coating materials of this invention set forth above to form coatings 12 and 14. A conductive lead wire 16 such as a copper wire is bonded to crystal 10 such as with solder 18 in order to input alternating electrical energy into crystal 10.

Figure 2:
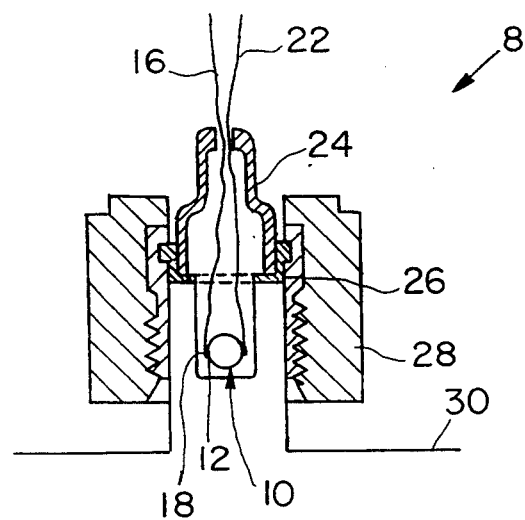
FIG. 2 is a top view of an apparatus of this invention.

Referring to FIG. 2, an apparatus of this invention is shown including the piezoelectric crystal 12 and connected to lead wire 16. A second lead wire 22 is bonded to crystal 10 which transmits vibration of the coated crystal to an electronic circuit such as described below. The electronic circuit monitors the frequency of vibration of the energized crystal. The coatings 12 and 14 are applied by an acceptable thin film deposition technique, e.g., sputtering. For the deposition of metal conductor, e.g., magnesium, DC sputtering is a possible mode. For other metals or metal hydrides, e.g., barium, strontium, RF is the recommended sputtering technique. In a process of utilizing an RF planar magnetron sputtering system for the deposition of barium, e.g., Model CrC-100 Planar Magnetron Sputtering System with optional 200 watt RF power supply manufactured by Plasma Sciences, Inc., a potential is applied to the barium target. In the sputtering process, the barium target will become negatively self-biased creating an enrichment of ions in front of the target. The ions strike the target and sputtering is obtained. The crystal is positioned on a pedestal located at a distance of one to three inches from the bottom of the sputtering head. The crystal is masked so deposition occurs only on the desired areas of the piezoelectric electrodes. Typical sputtering operations with this piece of equipment are performed at a pressure range of 2 to 10 mtorr and RF power of 80 to 150 W with argon as the sputtering gas. To eliminate oxidation of the deposited film, the entire sputtering process is conducted within a conventional glove box under argon.

The oscillator design is based on a CMOS Pierce Oscillator. The basic physics internal to the crystal is that of a sound wave propagating through the crystal. The initial electrical input at one voltage difference causes an expansion of the crystal. The initial voltage is produced by one end of the inverter gate due to its 180° phase difference from the other end of the inverter. The piezoelectric crystal behaves electrically like a high Q(quality) LC network, or physically like a mass spring. As the mass per unit length of the spring changes, so will the frequency of the springs oscillations. By changing the mass on the surface of the crystal frequency changes of the crystal oscillator can be detected.

Two CMOS Pierce Oscillators are used in the electronics circuit. One oscillator is used as a reference, the other as a mass sensor. The two signals are fed into a flip-flop that gives the difference frequency of the two crystals. This serves two purposes; one to null out any temperature effects, the other to give a smaller frequency value, e.g., 1,000,000 Hz reference signal, and 999,000 Hz sensor signal, will produce a 1,000 Hz difference frequency. The difference frequency is applied to a micro-controller counter input and frequency cycles summed for a given time period. Knowing the number of total cycles and the time period, frequency in Hz can be calculated. A ten second sample time gives 1/10 Hz resolution of the difference frequency.

Figure 3:
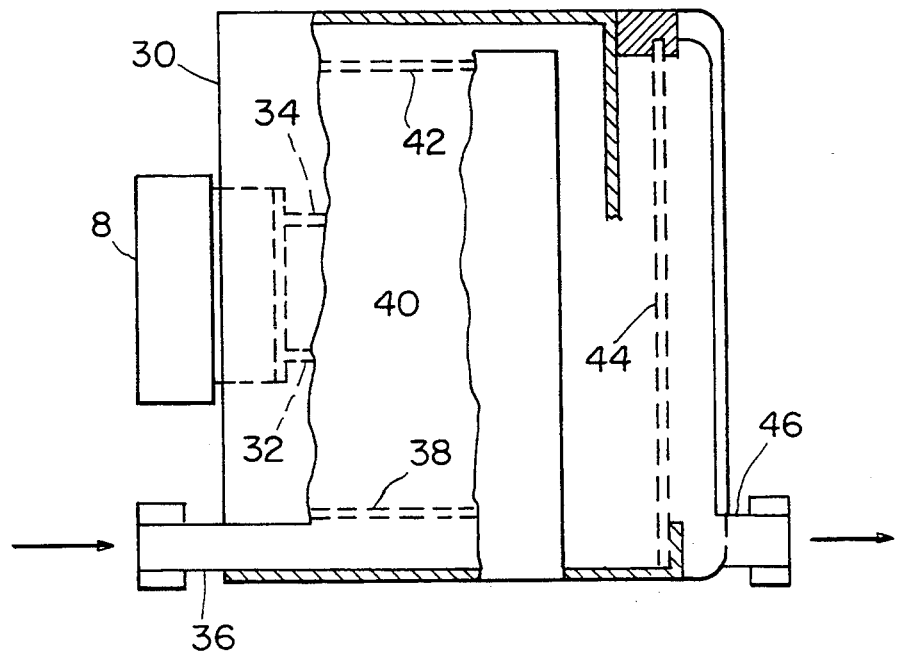
FIG. 3 is a schematic view illustrating the use of the apparatus of this invention.

Referring to FIG. 3, the sensor apparatus 8 of this invention is positioned on housing 30 and includes a gas inlet 32 and a gas outlet 34. Gas to be purified is introduced through inlet 36, through screen 38 and into resin bed 40. Optional resin bed 40 functions to scavenge oxygen and water vapor from the incoming gas. Purified gas is passed out screen 42, through final filter 44 and through outlet 46 to a zone for chemical reaction (not shown). Alternate device configurations are possible, including a device in which the coated crystal is mounted directly within the flowing gas stream.

The following examples illustrate the present invention and are not intended to limit the same.

EXAMPLE I

A device was assembled consisting of all stainless steel Swagelok$^R$ components to permit testing of coated quartz piezoelectric crystals. A ½" O.D. tube was used to contain ca. 3 mL of Waferpure ® gas purification resin via metal frits inserted into ¼" reducers. The downstream end of this tube was connected via a ¼" union tee to another ⅜" union tee via the appropriate reducers. An air-actuated bellows sealed valve was connected to the branch end of the ¼" union tee. The quartz crystal to be tested was inserted into the branch end of the ⅜" union tee using a vacuum feedthrough to permit connection of the lead wires to the external electronics. Two-way non-rotating stem valves on each end were used to seal the device from outside atmosphere when required.

All components, except the valves, were dried in a forced-air oven at 135° C. for 4 h, cooled to room temperature in a desiccator and introduced into a nitrogen-filled glove box. One of the gold electrodes of a 2.0-MHz quartz piezoelectric crystal was coated with ca. 80 ug of potassium metal and the crystal was inserted into the testing device. Upon removal from the glove box, the device was connected to a high purity test stand. Oxygen concentration was monitored by a Panametrics 1/$O_2$ detector.

The difference in frequency between the coated quartz crystal against a reference 2.0 MHz crystal was monitored over an 18-h period with data collection performed about every minute. A steady purge of Waferpure®-purified nitrogen gas was established through the device at 1.0 lpm (28 psig). About every five minutes the air-actuated valve would open to permit a twelve-second pulse of 12,000 ppm oxygen in nitrogen challenge gas at 30 lpm to the quartz crystal monitor.

Figure 4:
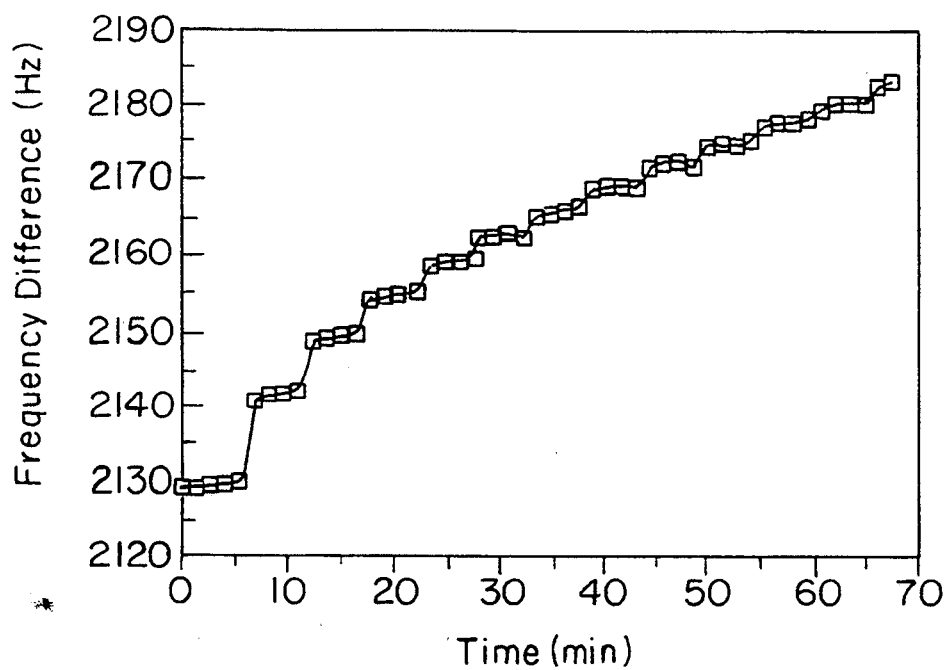
FIG. 4 shows the effect of air contact with the coated piezoelectric crystal device of this invention.

As shown in FIG. 4, the crystal responded in a stepwise fashion to the pulses of challenge gas. The frequency difference with respect to the reference crystal increased due to the mass increase from oxide formation on the crystal electrode.

EXAMPLE II

A device was assembled consisting of all stainless steel Swagelok$^R$ components to determine the effect of flow rate on a coated quartz piezoelectric crystals. The quartz crystal to be tested was inserted into the branch end of the ⅜" union tee using a vacuum feedthrough to permit connection of the lead wires to the external electronics. Two-way non-rotating stem valves were connected on each end of the straight path via ¼" reducers to seal the device from outside atmosphere when required.

All components were dried as described in Example I and introduced into a nitrogen-filled glove box. A 2.0-MHz quartz piezoelectric crystal (fo=2000.745 KHz) was coated with ca. 99 ug of potassium metal and the crystal was inserted into the testing device. Upon removal from the glove box, the device was connected to a high purity test stand. Oxygen concentration was monitored by a Panametrics 1/$O_2$ detector.

The difference in frequency between the coated quartz crystal against a reference 2.0-MHz crystal was monitored over an 4-h period with data collection performed about every minute. A challenge gas of 50 ppm oxygen in nitrogen was flowed through the device at 0.5 lpm for the first two hours, increased to 2.0 lpm for another two hours, then increased to 20.0 lpm for a few minutes.

Figure 5:
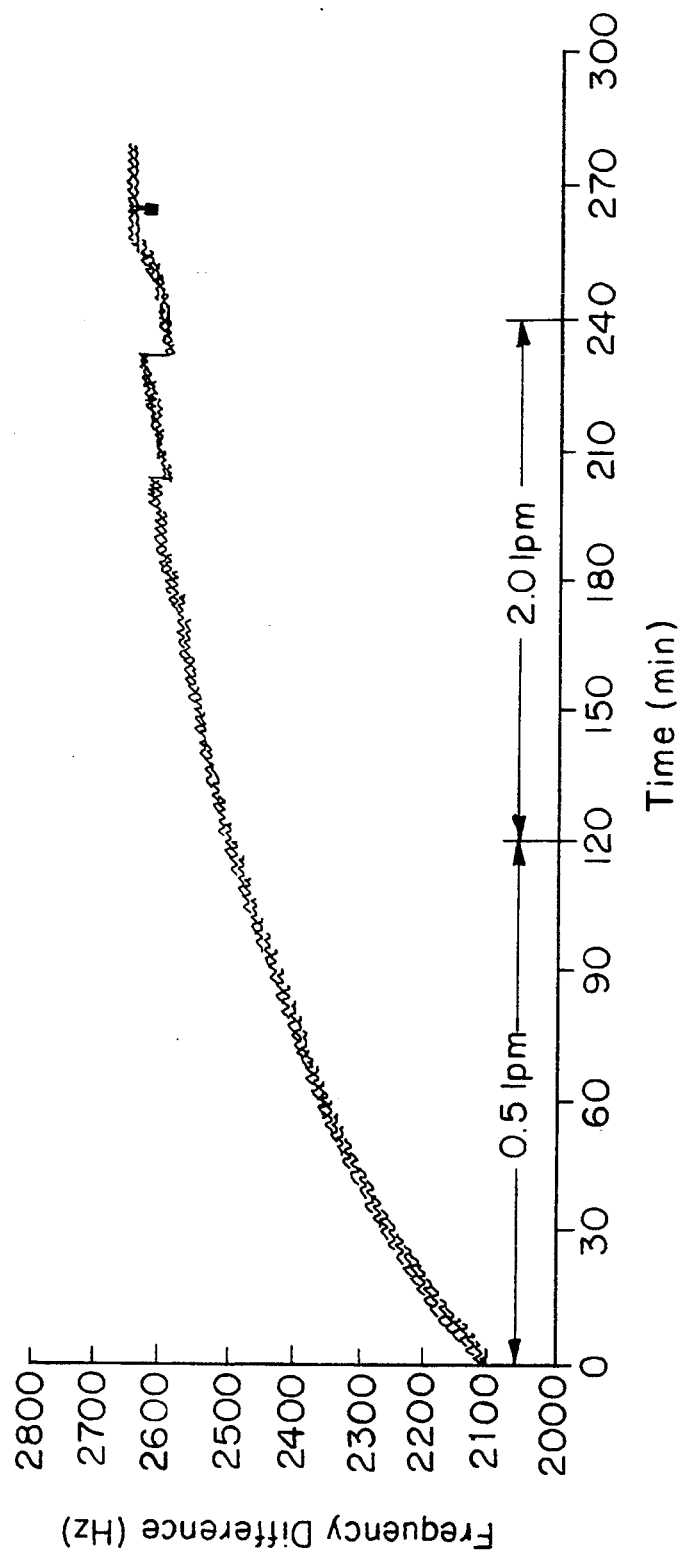
FIG. 5 also shows the effect of air contact with the coated piezoelectric crystal device of this invention.
Figure 6:
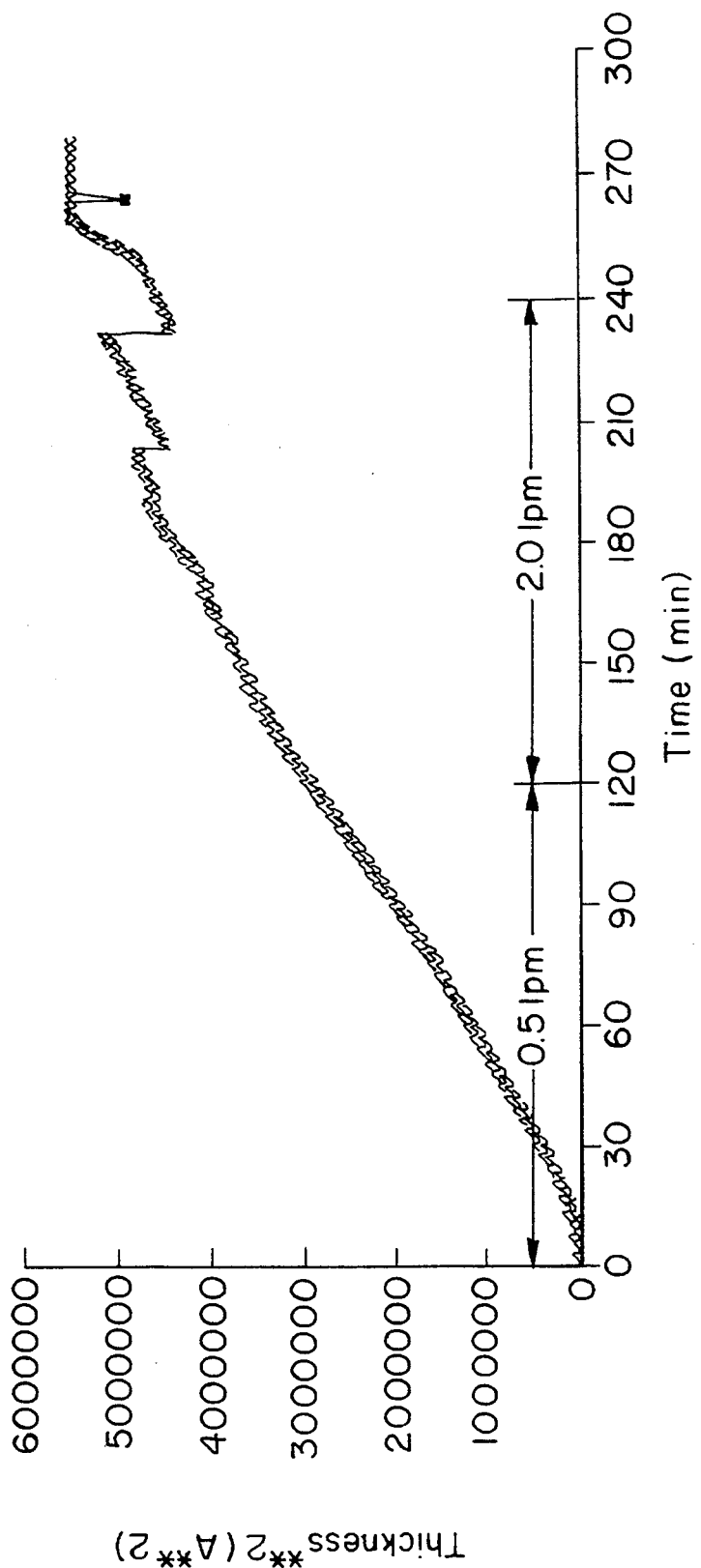
FIG. 6 shows the square of oxide growth thickness over time.

The change in crystal frequency over time is depicted in FIG. 5. If the change in frequency data is converted to a mass thickness change, then a plot of the square of the thickness vs. time provides a straight line as predicted by the parabolic growth law as shown in FIG. 6.

EXAMPLE III

A device was assembled consisting of all stainless steel Swagelok$^R$ components to determine the effect of flow rate on a coated quartz piezoelectric crystal in a filter housing. The quartz crystal to be tested was inserted into a ⅜" tee type removable filter housing using a vacuum feedthrough to permit connection of the lead wires to the external electronics. Two-way non-rotating stem valves on each end were used to seal the device from outside atmosphere when required.

The components were dried as described in Example I and introduced into a nitrogen-filled glove box. A 2.0-MHz quartz piezoelectric crystal with Ag/Cr electrodes (fo=1999.637 KHz) was coated with ca. 134 ug of strontium metal distributed between the two electrodes and the crystal was inserted into the filter housing. Upon removal from the glove box, the device was connected to a high purity test stand. Oxygen concentration was monitored by a Panametrics 1/$O_2$ detector.

Figure 7:
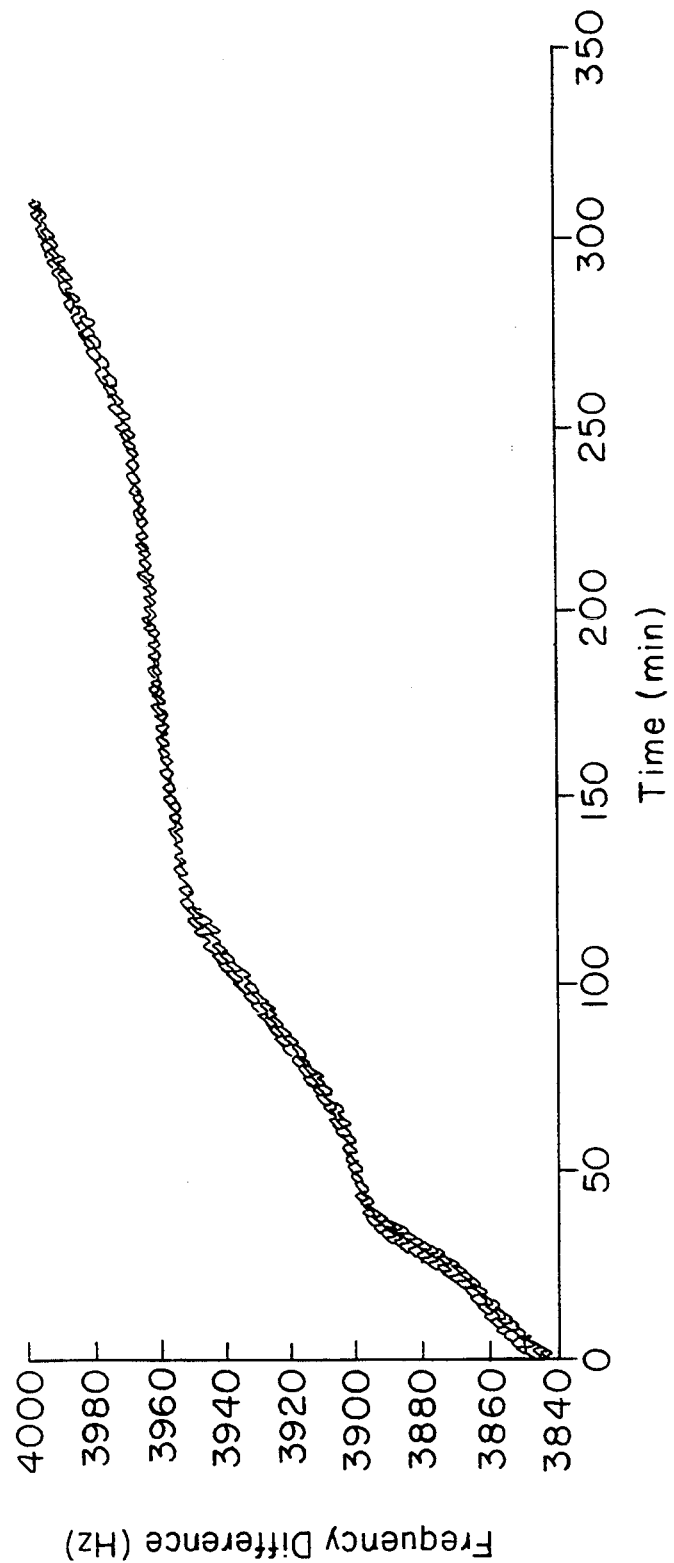
FIG. 7 shows the effect of flow rate on frequency difference of strontium coated 2.0 MHz quartz piezoelectric crystal in a filter housing as a function of time.

The flow rate of a 20 ppm oxygen in nitrogen challenge gas was alternated between 0.1 and 1.0 lpm to determine the effect of flow rate through the filter housing design. The response of the crystal is shown in FIG. 7.

We claim:

1. A sensing device for measuring a first composition selected from the group consisting of oxygen, water and mixtures thereof in a stream of purified gases which comprises:

a piezoelectric material having a surface with an effective mass of a coating applied to said surface of said piezoelectric material, said coating formed of a second composition selected from the group consisting of a pure metal, a metal hydride and mixtures thereof; said second composition being reactive with said first composition to form a product selected from the group consisting of an oxide, a hydroxide and mixtures thereof, said coating having a mass which permits said piezoelectric material to vibrate in response to electrical current, means for applying an alternating electrical current to said piezoelectric material and means for measuring frequency of vibration of said piezoelectric material.

2. The device of claim 1 wherein said material has said coating on two opposing surfaces.

3. The device of claim 1 wherein said piezoelectric material is quartz.

4. The device of claim 2 wherein said piezoelectric material is quartz.

5. The device of claim 1 wherein said coating is barium.

6. The device of claim 2 wherein said coating is barium.

7. The device of claim 3 wherein said coating is barium.

8. The device of claim 4 wherein said coating is barium.

9. The device of claim 1 wherein said coating is magnesium hydride.

10. The device of claim 2 wherein said coating is magnesium hydride.

11. The device of claim 3 wherein said coating is magnesium hydride.

12. The device of claim 4 wherein said coating is magnesium hydride.

13. The device of claim 1 wherein said coating is lithium hydride.

14. The device of claim 2 wherein said coating is lithium hydride.

15. The device of claim 3 wherein said coating is lithium hydride.

16. The device of claim 4 wherein said coating is lithium hydride.

17. The device of claim 1 wherein said coating is lithium.

18. The device of claim 2 wherein said coating is lithium.

19. The device of claim 3 wherein said coating is lithium.

20. The device of claim 4 wherein said coating is lithium.

21. The device of claim 1 wherein said piezoelectric material is poly(vinylidene fluoride).

22. The device of claim 2 wherein said piezoelectric material is poly(vinylidene fluoride).

23. The device of claim 1 wherein said coating includes a protective material comprising poly(vinylidene fluoride).

24. The device of claim 1 wherein said coating includes a protective material comprising polytetrafluoroethylene.

25. The device of claim 2 wherein said coating includes a protective material comprising poly(vinylidene fluoride).

26. The device of claim 2 wherein said coating includes a protective material comprising polytetrafluoroethylene.

* * * * *